(12) United States Patent
Brown (10) Patent No.: US 10,945,886 B2
(45) Date of Patent: *Mar. 16, 2021

(54) EYE MARKER DEVICE WITH ELECTRONIC POSITIONAL DETECTION SYSTEM AND TIP ASSOCIATED THEREWITH

(71) Applicant: Mindskid Labs, LLC, Wilmington, NC (US)

(72) Inventor: Alan Wesley Brown, Wrightsville Beach, NC (US)

(73) Assignee: Mindskid Labs, LLC, Wilmington, NC (US)

(*) Notice: Subject to any disclaimer, the term of this patent is extended or adjusted under 35 U.S.C. 154(b) by 214 days.

This patent is subject to a terminal disclaimer.

(21) Appl. No.: 16/241,037

(22) Filed: Jan. 7, 2019

(65) Prior Publication Data

US 2019/0240072 A1 Aug. 8, 2019

Related U.S. Application Data

(63) Continuation of application No. 14/259,537, filed on Apr. 23, 2014, now Pat. No. 10,201,454.

(60) Provisional application No. 61/927,754, filed on Jan. 15, 2014, provisional application No. 61/815,020, filed on Apr. 23, 2013.

(51) Int. Cl.
*A61F 9/013* (2006.01)
*A61B 34/20* (2016.01)
*A61B 90/00* (2016.01)

(52) U.S. Cl.
CPC .... *A61F 9/0136* (2013.01); *A61B 2034/2048* (2016.02); *A61B 2090/395* (2016.02)

(58) Field of Classification Search
CPC ........ A61F 9/009; A61F 9/013; A61F 9/0133; A61F 9/0136; A61F 2009/00872; A61B 2019/545; A61B 2019/5245; G02B 23/14; G02B 23/105
USPC .................................. 606/161, 166
See application file for complete search history.

(56) References Cited

U.S. PATENT DOCUMENTS

| | | | |
|---|---|---|---|
| 10,201,454 B2* | 2/2019 | Brown | A61F 9/0136 |
| 2012/0245609 A1* | 9/2012 | Brown | A61F 9/0136 606/166 |
| 2012/0293643 A1* | 11/2012 | Hanna | H04N 5/23212 348/78 |

* cited by examiner

*Primary Examiner* — Wade Miles
*Assistant Examiner* — Kankindi Rwego
(74) *Attorney, Agent, or Firm* — Williams Mullen; F. Michael Sajovec (57) ABSTRACT

The present invention provides methods and systems for an eye marker device that includes a handle and an eye marker tip, wherein the eye marker tip includes at least two arms dimensioned for placing at least one mark or indicator on a cornea, sclera or sclera/cornea junction.

14 Claims, 11 Drawing Sheets

EYE MARKER DEVICE WITH ELECTRONIC POSITIONAL DETECTION SYSTEM AND TIP ASSOCIATED THEREWITH

CROSS-REFERENCE TO RELATED APPLICATIONS

This application is a continuation of U.S. Utility application Ser. No. 14/259,537 filed on Apr. 23, 2014 that claims the benefit of the earlier priority filing date of U.S. Provisional Patent Application No. 61/927,754, filed on Jan. 15, 2014 and U.S. Provisional Patent Application No. 61/815,020, filed on Apr. 23, 2013, the disclosures of which are incorporated herein by reference as if set forth in their entireties.

FIELD OF THE INVENTION

The present invention relates generally to an eye marker device and tip and more generally relates to an eye marker device with an electronic positional detection system and a tip associated therewith.

BACKGROUND OF THE INVENTION

The current invention addresses the problem of long lasting accurate ink marks applied to the ocular surface as needed for the correction of astigmatism.

In the field of refractive surgery there exists a need to place ink marks on the eye in order to orient the treatment of astigmatism. Astigmatism is a condition where the shape of the cornea bends light to more than one focal point causing a blurred image upon the retina. Astigmatism caused by the cornea is described as corneal astigmatism or corneal cylinder. It can be treated by altering the shape of the corneal through incisions or laser means so the light entering the eye is refracted to one focal point. Alternatively, in the field of cataract surgery, the corneal astigmatism can be balanced by an intraocular toric lens implant that has a curved surface that counterbalances the corneal astigmatism. Regardless of the means of treatment of astigmatism, the eye has to be marked before surgery in order to properly position the treatment of the astigmatism.

The current means of marking the eye generally involves the use of metal corneal markers. In most cases the metal marker has projections that will touch the cornea or sclera. Ink from a sterile surgical marker is transferred from the ink marker to the projections of a sterilized metal marker. This thin layer of ink is then transferred to the eye by compressing the metal marker projections against the anesthetized cornea. All markers currently used suffer from issues of inadequate ink transfer to the eye surface principally due to the fact that only a thin layer of ink is being transferred to an ocular surface and that wet from the ocular tear film. The ink marks so placed are blinked off within minutes. Because the marks are so short lived they must be placed immediately before the onset of surgery.

All patients are now required to have the operative site marked with a surgical marker before being brought into the operating room. A review of the general steps used to mark a patients eye before surgery will help better understand the full extent of the challenges facing the surgeon and patient.

Sequence Option 1—Marking in the Operating Room
 1. After the patient has been sedated and has been marked over the operative eye brow, they are brought into the operating room on a stretcher reclined at about 30-45 degrees.
 2. The patient is then asked to sit up as straight as possible for the surgeon to mark the eye with an inked sterile metal marker that has marking fins rotated to the desired astigmatic axis.
 3. The patient then lies down and is prepped and draped for surgery with marks in the proper position for surgery.

It is well known that the position of the eye rotates or undergoes cyclotorsion when the patient moves from a vertical or sitting position to a lying or supine position. Errors induced by supine marking can be up to 20 degrees which results in a dramatic reduction in the effectiveness of the astigmatism correction. Consequently, the eye must be marked with the patient in the sitting or vertical position since this is the normal position of use for the eyes. This requirement conflicts with the typical operating room sequence of having the patient lying down, prepped, draped and ready for the surgeon before the surgeon enters the operating room. The need for the patient to be marked in the sitting position by the surgeon delays the normal prep sequence for surgery. An alternative sequence is to have the patient pre-marked in another patient preparation area where oral sedation is administered. The pre-marking is done with a surgical ink marker applied to the area where the cornea meets the sclera. These markers leave a lasting residue of ink not found with the thin film of ink applied with sterile metal markers. The sequence in these cases is as follows:

Sequence Option 2—Marking in Preoperative Area:
 1. Patient is asked to sit up straight and fixate on a distant object.
 2. The surgical marker is applied to the eye in the horizontal and, when possible, vertical meridians. These marks serve as reference marks to identify the eye position when the patient is upright.
 3. Once the remainder of the patient preparation is accomplished the patient is moved to the operating room where they are placed in the supine position and then prepped and draped for surgery.
 4. The surgeon begins by identifying the previously placed reference surgical marker marks that were placed on the eye when the patient was upright.
 5. A sterile metal marker that has been inked is used with the previously placed reference marks to properly place the astigmatic axis marks of the sterilized metal marker.

This sequence is more efficient because surgeons are required now to mark the patient's brow over the eye having surgery prior to being moved to the operating room. Because every patient gets marked with a surgical marker over the brow, it is convenient for the surgeon to add marks on the eye at the same time. Metal markers retain only a thin film of ink that is blinked off within a few minutes and consequently, they cannot be used for marking outside of the operating room.

Clearly the above system to mark the eye for the treatment of astigmatism is complex and creates limitations as to the accuracy of the marks placed, how the procedure is performed and how the patient flow is achieved. In order to alleviate the above disadvantages the current invention is presented herein.

The advantages of an eye marking device and tip, with a pre-inked, sterile, optionally disposable marking apparatus that is positioned using an automatic electrical positional detection system can be better appreciated better through the accompanying illustrations and description below.

SUMMARY OF THE INVENTION

According to an embodiment of the present invention, an eye marker device comprises a handle, a tip engaged to the handle and includes a marking means with at least one arm containing a marking apparatus, a rotational scale, and a servo motor.

According to another embodiment of the present invention, an eye marker device that includes an open end on the handle for receiving a post of the tip for forming a selectively secured arrangement.

According to yet another embodiment of the present invention, an eye marker device that includes a marking means of the tip that comprises a middle portion and two spaced-apart arms extending from the middle portion.

According to yet another embodiment of the present invention, an eye marker device that includes a tip with a post extending therefrom and a hollow rod within the handle. The post is received within the hollow rod for forming a selectively secured arrangement between the tip and the handle.

According to yet another embodiment of the present invention, an eye marker device that includes at least one battery for providing power to an LED.

According to yet another embodiment of the present invention, an eye marker device that includes a tip composed of a transparent plastic.

According to yet another embodiment of the present invention, an eye marker device that includes an accelerometer, level sensor, and position sensor.

According to yet another embodiment of the present invention, an eye marker device that includes a hollow rod disposed within the handle with a weight rotationally engaged to the hollow rod.

According to yet another embodiment of the present invention, an eye marker device that includes a hub on the anterior end of the handle for receiving a cavity formed within the base of the tip.

According to yet another embodiment of the present invention, a tip that includes a base with a first side and a second side and extends to an outer edge, a marking means extending from the first side of the base that comprises a middle portion with a top portion and at least one arm extending above the top portion of the middle portion, and a post extending from the second side of the base.

According to yet another embodiment of the present invention, a tip that has an annular ring with an internal side and an external side that extends from the outer edge and forming a cavity within the internal side of the annular ring and bottom portion of the base.

According to yet another embodiment of the present invention, a tip that has a base with a centrally located bore and the post is positioned over the bore.

According to yet another embodiment of the present invention, a tip that has two arms positioned on opposed sides of the middle portion and extend outwardly from the middle portion.

According to yet another embodiment of the present invention, a tip that has at least one ridge extending from the marking apparatus.

According to yet another embodiment of the present invention, an eye marker device that includes an adaptor with an electrical plug, an elongate housing, a rotational scale, and a marking apparatus aligned with a position indicator.

According to yet another embodiment of the present invention, an eye marker device that includes a post on either side of the electrical plug.

According to yet another embodiment of the present invention, an eye marker device that includes a rotational turret on the adaptor.

According to yet another embodiment of the present invention, an eye marker device that includes at least one arm extending outwardly from the adaptor.

According to yet another embodiment of the present invention, an eye marker device that includes a marking apparatus engaged to an end of at least one arm extending outwardly from the adaptor.

BRIEF DESCRIPTION OF THE DRAWING

The present invention is illustrated and described herein with reference to the various drawings, in which like reference numbers denote like method steps and/or system components, respectively, and in which.

DETAILED DESCRIPTION OF INVENTION

The present invention may be understood more readily by reference to the following detailed description of the invention taken in connection with the accompanying drawing figures, which form a part of this disclosure. It is to be understood that this invention is not limited to the specific devices, methods, conditions or parameters described and/or shown herein, and that the terminology used herein is for the purpose of describing particular embodiments by way of example only and is not intended to be limiting of the claimed invention. Any and all patents and other publications identified in this specification are incorporated by reference as though fully set forth herein.

Also, as used in the specification including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

Figures 1A, 1B:
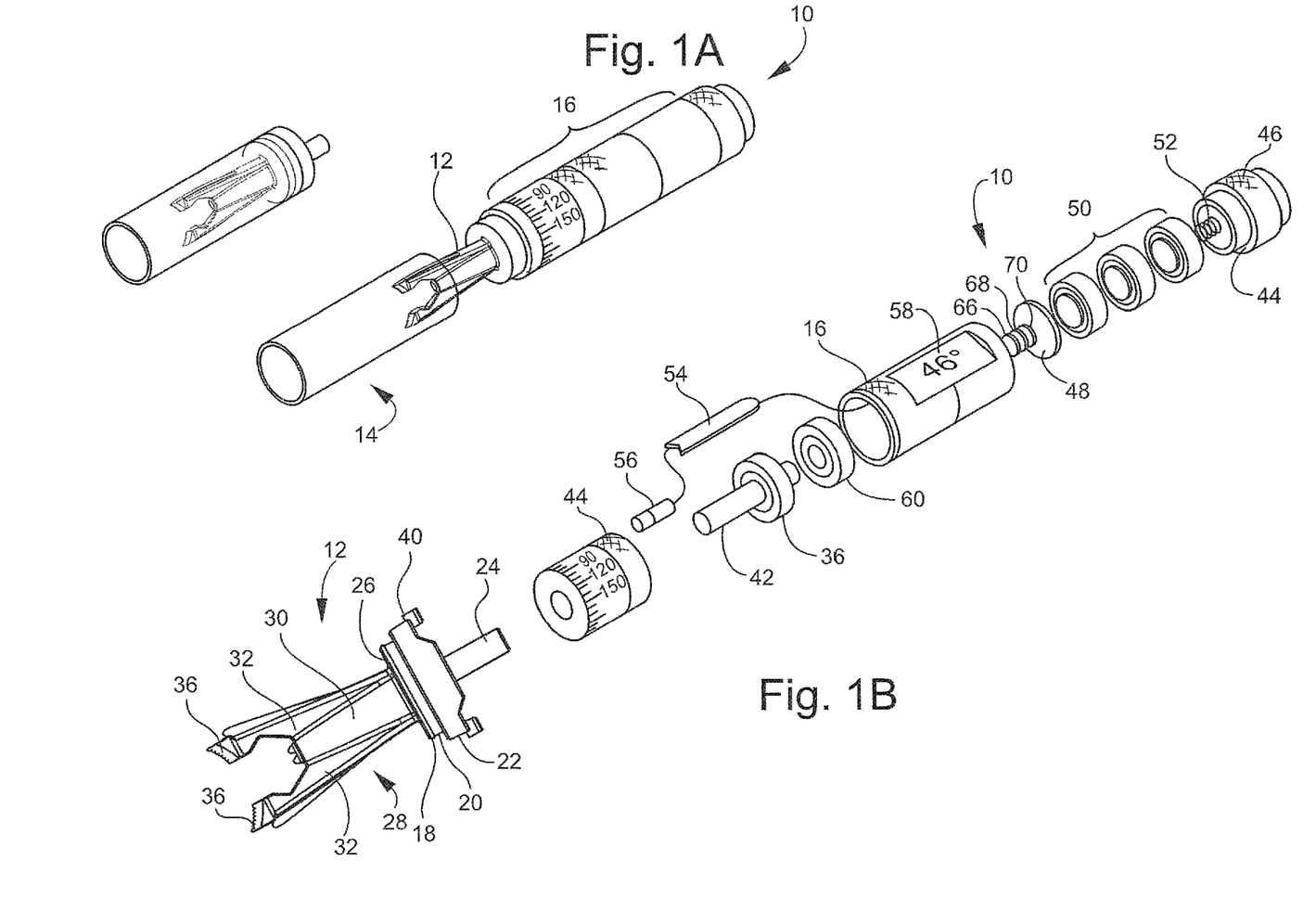
FIG. 1A is a perspective view of the eye marker device with an electronic positional detection system.
FIG. 1B is an exploded view of the eye marker device with an electronic positional detection system.

Referring now specifically to the drawings, an eye marker device is illustrated in FIG. 1 and is shown generally at reference numeral 10. The device 10 comprises a tip 12 with an optional sleeve 14 that is engaged to a handle 16. The handle 16 contains a cavity for receiving, protecting, and containing the internal components of the device 10. The handle 16 may also contain an open end for receiving a post 24 of the tip 12 forming a selectively secured arrangement.

Figure 2:
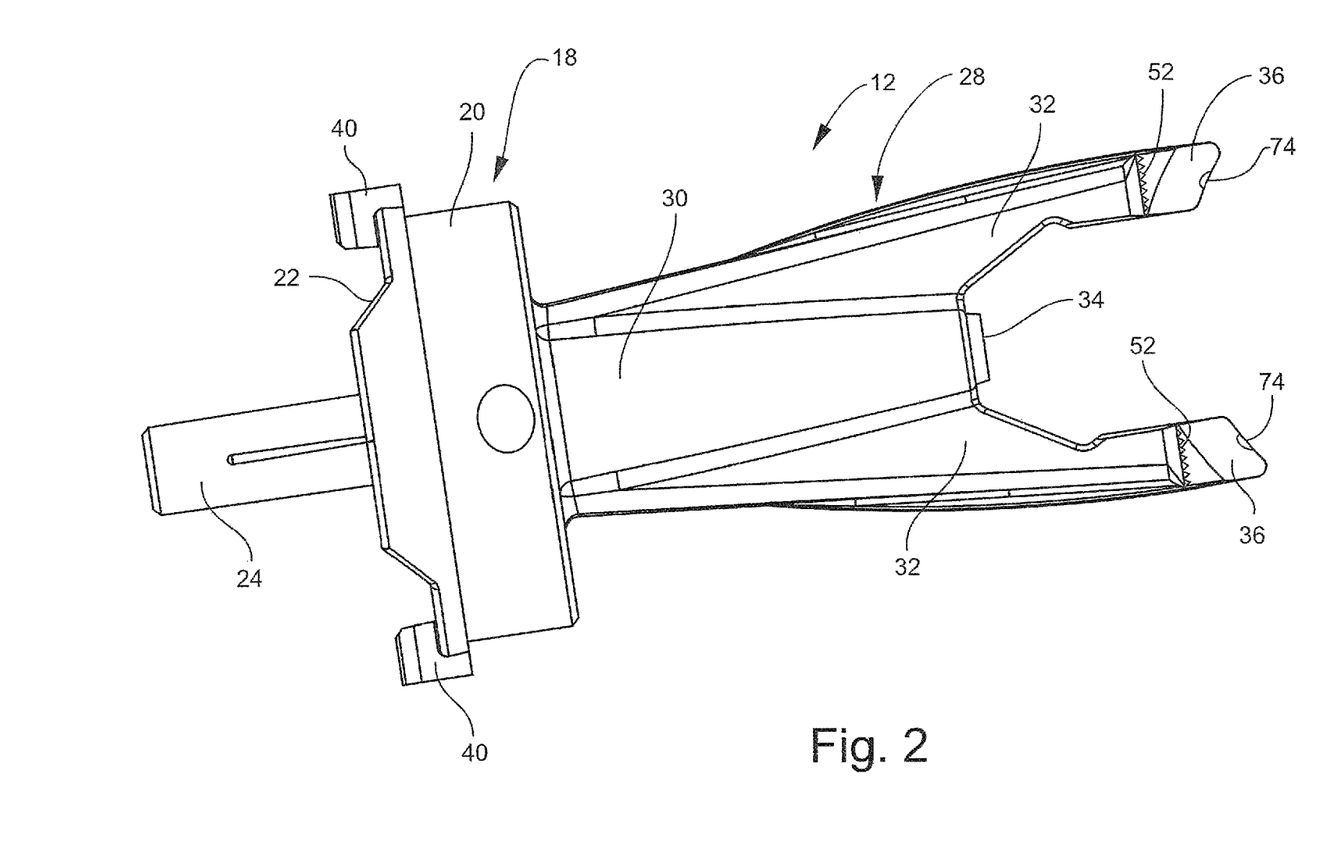
FIG. 2 is a perspective view of one embodiment of the tip.
Figure 3:
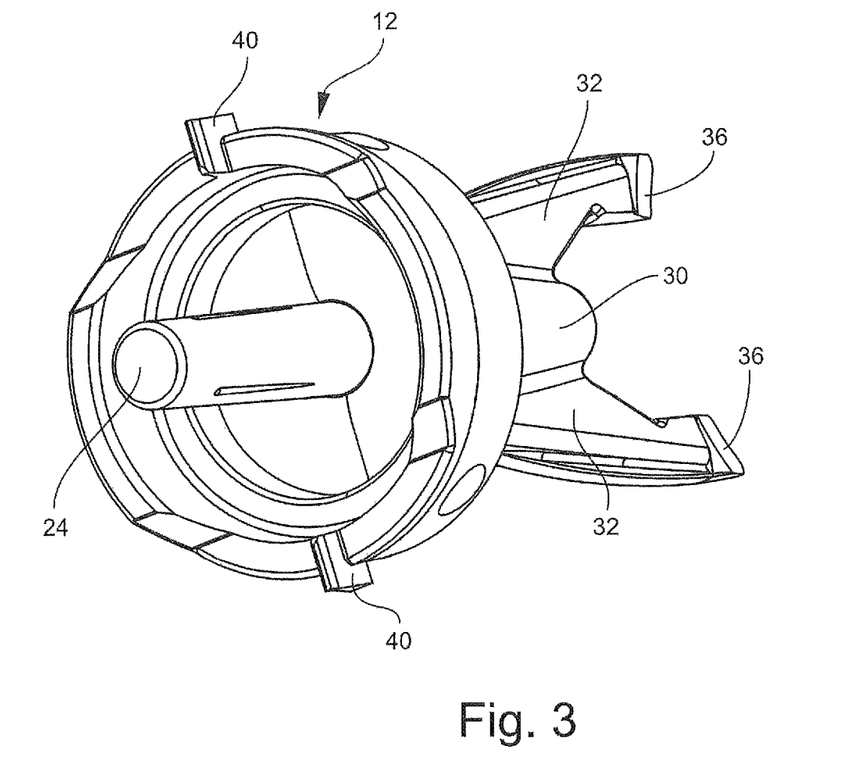
FIG. 3 is a bottom perspective view of one embodiment of the tip
Figure 4:
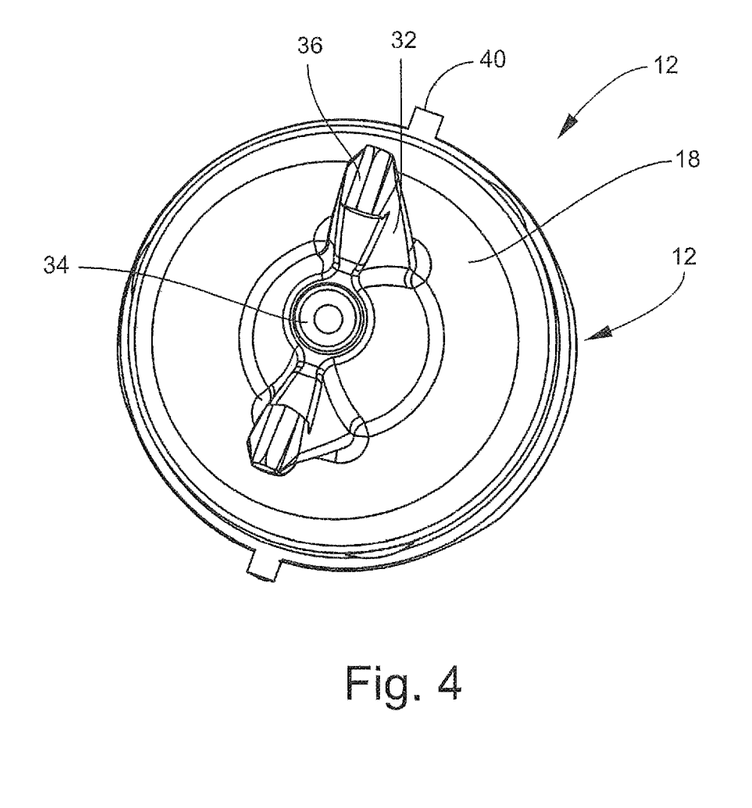
FIG. 4 is a top perspective view of one embodiment of the tip.
Figure 5:
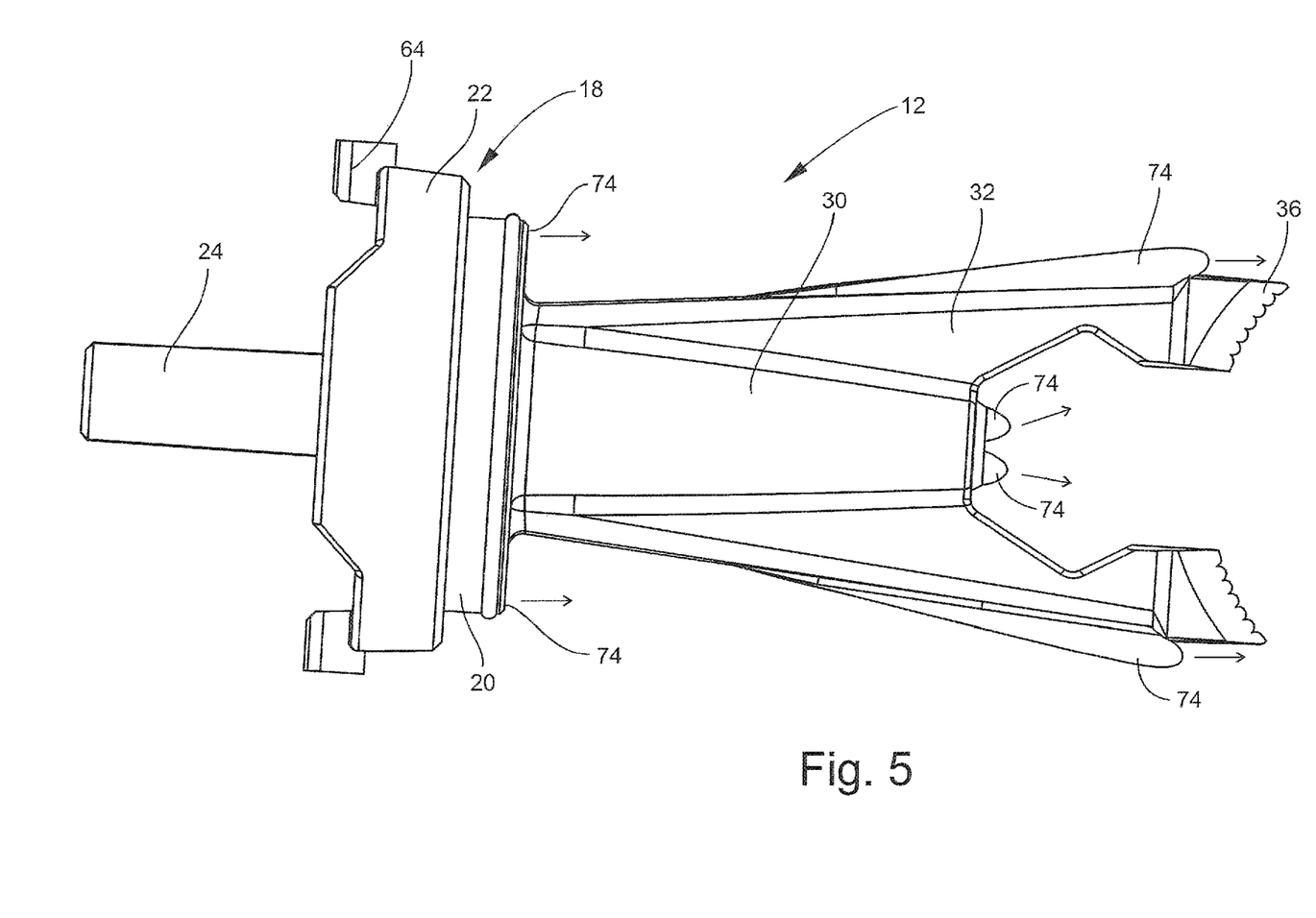
FIG. 5 is a perspective view of another embodiment of the tip.
Figure 6:
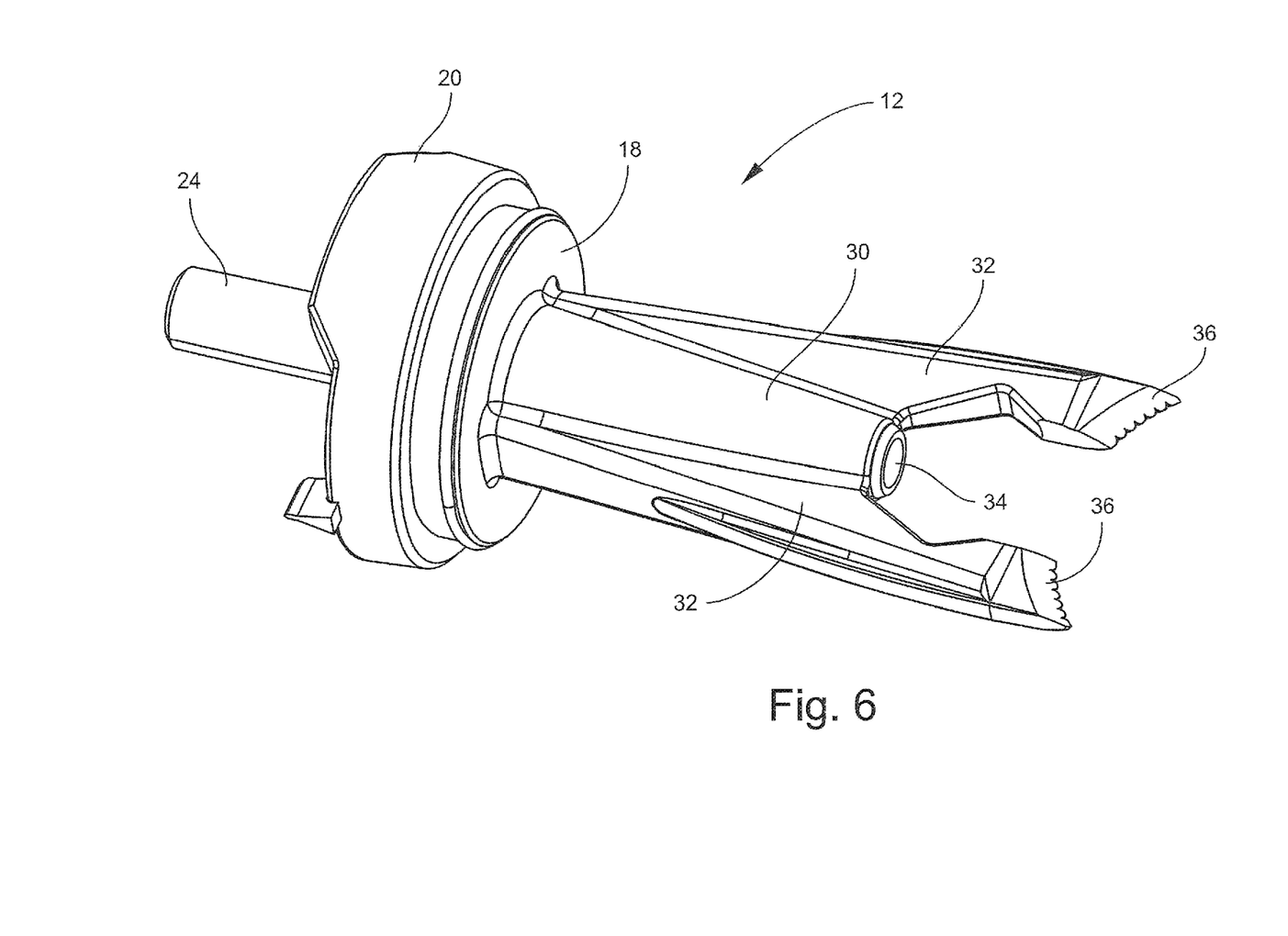
FIG. 6 is another perspective view of another embodiment of the tip.

As illustrated in FIGS. 1A, 1B, 2, 3, 4, 5, and 6, the tip 12 may be housed within the sleeve 14. The sleeve 14 has a closed end and an open end. The tip 12 comprises a base 18 with a first side and a second side that extends to an outer edge. An annular ring 20 having an interior side and exterior side are engaged to the outer edge of the base 18 and extending generally downward from the second side of the base 18 forming a cavity within the internal side of the annular ring and the bottom portion of the base 18. The external side of the base 18 comprises a rim 22 that circumscribes the external side of the base 18, extending generally upwardly from the external side of the base 18. A post 24 extends from the base 18. The post 24 may be generally circular and hollow and having atop side and the bottom side. The post 24 may also be solid. The top side of the post 24 is engaged to the second side of the base 18 and extending generally outward therefrom. The post 24 is preferably engaged to the central portion of the base 18. The base 18 may contain a centrally located bore 26 that extends from the first side to the second side of the base 18. The post 24 is engaged to the second side of the base 18 and overtop the bore 26 in the base 18 for allowing light to pass through the post 24 and proceed through the bore 26. The tip 12 includes a marking means 28 is engaged to the first side of the base 18. The marking means 28 comprises a generally conical middle portion 30 and at least one arm 32 extending therefrom. As illustrated in FIGS. 2 and 5, at least two arms 32 extend from the middle portion 30 and extend outward from the middle portion 30 and extend above the middle portion 30. The arms 32 as illustrated are positioned on either side of the middle portion 30 and in a spaced apart relationship. The middle portion 30 is preferably hollow or has a central passageway for allowing light to progress through the middle portion 30. The middle portion 30 has a top portion and a bottom portion. The bottom portion of the middle portion 30 is engaged to the first side of the base and extends generally outward therefrom. As illustrated, the diameter of the middle portion gradually decreases from the bottom portion to the top portion. A lens 34 may optionally be positioned within a centrally located opening within the top portion of the middle portion 30, or may alternatively be placed at the base of post 24.

The middle portion 30 contains an external side and an internal side. The arms 32 extend outwardly from the external side of the middle portion 30 and longitudinally upward and extending above the middle portion 30. The arms 32 are spaced apart for allowing light to pass out of the top portion of the middle portion 30 and not obstructed by the arms 32. The upper portion of the arms 32 consist of a marking apparatus 36, or may alternatively be placed at the base of the post 24.

The sleeve 14 protects the tip 12, including the marking apparatus 36, from exposure during shipment and assembly. The marking apparatus 36 may be pre-inked, whereby the tip is infused with ink prior to shipment to the user and the user does not constantly have to apply ink to the marking apparatus 36. Additionally, the marking apparatus 36 may be used repetitively, if necessary, on the same patient for providing more than one mark without having to constantly apply ink. Alternatively, the marking tip 36 may apply a tack or other like indicator on the surface of the cornea, sclera, or the sclera/cornea junction.

The marking apparatus 36 is shown in more detail in FIGS. 2 and 5: The marking apparatus 36 may be selectively secured to the arm 32. The arm 32 may include biased retention members 52, as shown in FIG. 2, for selectively securing the marking apparatus 36 to the arm 32. The post 24 may itself be a biasing member by having a coil spring, leaf spring, or other similar compressive configuration within the post 24. The biased retention member 52 may be spring loaded and depress within the arm 32 when pressure is applied to the marking apparatus 36. The purpose of the biased retention member 52 is to depress when pressure is applied to the marking apparatus 36. Alternatively, the biased retention member 52 may be located within the body of the arm 32. The compression or damping effect caused by the biased retention element 52 or damping element allows the patient to be more comfortable during the procedure and allows a "soft touch" to the exterior of the eye. The biased retention element 52 or damping element may be engaged to the device in a multitude of ways.

The marking apparatus 36 may also contain any material containing a formed indicator reservoir or a channel with passive flow to the surface. The marking apparatus 36 may be of any material with nanotubules/channels or the like or with a material containing pigment/indicator encapsulated microbeads/granules that are able to release the indicator upon contact with pressure, water, the tear film, heat, or other release mechanism. Further, the marking apparatus 36 may contain a microprint cartridge like mechanism where the indicator is jetted from the marking apparatus 36 in a favorable pattern by an electronic or non-electronic mechanism. The marking apparatus 36 may contain or be attached to a compressible reservoir of indicator/ink such that compression forces the indicator/ink to the surface of the marking apparatus 36. The marking apparatus 36 may be coated with a biocompatible glue or gel that is itself covered with the indicator/ink such that the glue or gel acts as an adhesive to keep the indicator/ink attached to the marking apparatus 36 and such that the indicator/ink constitutes the external surface of the marking tip/glue/gel complex, or the marking apparatus 36 may be a biocompatible glue or gel that is mixed with the indicator such that the composite of the glue/gel/indicator/ink constitutes the external surface of the nib. The device 10 may also consist of a releasing agent that may release ink onto the eye by compression. The ink is bound to the marking apparatus 36, and once compression or a pressure is applied to the marking apparatus 36 and ink, the ink is transferred onto the eye. The marking apparatus 36 may be inked in gentian violet ink or a infrared ink, such as indocyanine green.

A position indicator 40 is disposed on the exterior side of the annular ring 20. The position indicator 40 may be placed on the exterior side of the annular ring 20. Alternatively, the position indicator 40 may be a groove that is pigmented. The position indicator 40 as illustrated consists of a marking or arrow for providing a visual representation.

A hollow rod 42 is located on the proximal end of the handle 16 and is rotationally engaged to a rotational scale 44 via a centrally located bore. The hollow rod 42 and rotational scale 44 may be one integral unit, or in the alternative, the hollow rod 42 is removable and slidable within the centrally located bore of the rotational scale 44. An activation mechanism 46 is located at the most distal end of the handle 16. The activation mechanism 46 may be rotated, clicked, or otherwise manipulated to activate and deactivate a light source, such as an LED 48 disposed on the enclosed electrical circuit. The activation mechanism 46 is electrically engaged to the LED 48 for turning the LED 48 "on" or "off" by supplying power and cutting off power to the LED 48. At least one battery 50 is positioned within the handle 16 and supplies the necessary power to power the LED 48. The battery 50 may be single use or rechargeable. The device 10 may be engaged to a recharging base for recharging the battery 50. A biasing element 52 is disposed between the activation mechanism 46 and the battery 50 for exerting a force upon the battery 50. The light from the LED 48 is transmitted through a hollow core of the hollow rod 42 that passes through the post 24, base 18, and proceeds outward from the hollow rod 42 that passes through the post 24, base 18, and proceeds outward from the middle portion 30. Alternatively, the hollow rod 42, post 24, base 18, and middle portion 30 can be made of clear or translucent plastic or the like, allowing light from the LED 48 to pass through the device 10.

The device 10 contains an electronic positional detection system that includes a circuit 54 with an accelerometer 66, level sensor 68, and position sensor 70. A servo motor 56 is engaged to the rotational scale 44 for rotating the rotational scale 44. In another alternative embodiment, the rotational scale 44 may be disposed on the annular ring 20 of the base 18. A display 58 is in communication with the servo motor 56 for activating and positioning the servo motor 56 to the desired axis. As mentioned above, the battery 50 provides power to the LED 48 and an activation mechanism 46 turns the LED 48 "on" or "off." The circuit 54 may also include a timer that prevents the flow of electricity to the LED 48 and turns the LED 48 "off." The timer can have a predetermined time limit to prevent the flow of electricity. For instance, the timer may allow the flow of electricity, wherein the LED 48 is "on", and after five minutes, the flow of electricity ceases to the LED 48 and the light is turned "off." Additionally, a timer or like mechanism may be included within the electrical circuit allowing the LED 48 to blink or turn "on" and "off" periodically. The LED 48 may be designed to mimic the fixation light commonly used in ophthalmic diagnostic equipment in a manner that would be known to others of ordinary skill in the art. Alternatively, the LED 48 may be a ANSI eye safe laser LED. The ANSI eye safe laser LED may yield a laser projection from a marking apparatus opening 74, which is an opening in an area adjacent or in close proximity to the marking apparatus 36 as it closes in on the eye surface. Consequently, the user would know where the marks from the marking apparatus 36 would be left before the actual landing of the marking apparatus 36 onto the eye thereby giving the user an opportunity to change the path of the marking apparatus 36 for a more favorable marking location. Alternatively, and as illustrated in FIG. 5, the opening 74 may be positioned on the top portion of the middle portion 30, forming a divergent laser optic, the opening 74 may be positioned on the upper portion of the arms 32, or the opening 74 may be positioned on the first side of the base 18. As illustrated in FIG. 5, the opening 74 may be positioned on the upper portion of each arm 32. The opening 74 may be positioned an equal distance part on the first side of the base 18 and spaced-apart from the outside diameter of the arms.

If needed, the circuit 54 of the device 10 is tared or "zeroed" with respect to a known horizontal or vertical plane. The user can adjust the marking disk 18 to a correct axis manually on the rotational scale 44 or the user may enter the desired degree or angle for the tip 12 using the display 58. The circuit 54 activates the servo motor 56 causing the tip 12 to be positioned at the desired axis and supplies power to the LED 48. Any position change of the device 10 is sensed by, the circuit 54 and then automatically repositions the servo motor 56 and tip 12 to maintain the tip 12 on the desired axis. Consequently, no matter what position the device 10 is turned, the circuit 54 instantly repositions the tip 12 to the correct axis position. An optional weight 60 may be included and rotationally engaged to the hollow rod 32 for providing additional balance for the tip along the horizontal axis.

Figure 7:
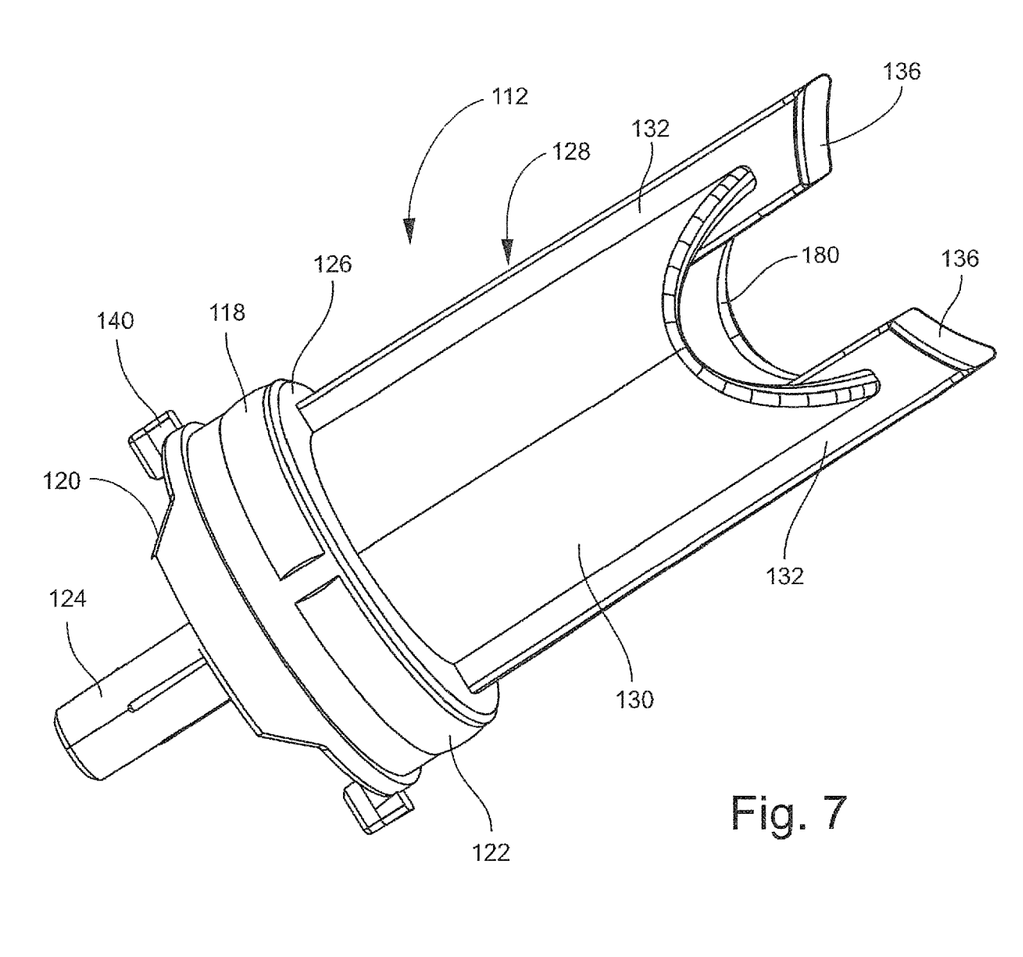
FIG. 7 is another perspective view of another embodiment of the tip.

In an alternative embodiment of the present invention as illustrated in FIG. 7, the tip 112 comprises a base 118 with a first side and a second side that extends to an outer edge. An annular ring 120 having an interior side and exterior side is engaged to the outer edge of the base 118 and extending generally downward from the second side of the base 118 forming a cavity within the internal side of the annular ring and the bottom portion of the base 118. The external side of the base 118 comprises a rim 122 that circumscribes the external side of the base 118, extending generally upwardly from the external side of the base 118.

A post 124 extends from the base 118. The post 124 may be generally circular and may be hollow or made of a solid clear plastic and having a top side and the bottom side. The top side of the post 124 is engaged to the second side of the base 118 and extending generally outward therefrom. The post 124 is preferably engaged to the central portion of the base 118. The base 118 may contain a centrally located bore 126.

The tip 112 includes a marking means 128 is engaged to the first side of the base 118. The marking means 128 comprise a generally cylindrical middle portion 130 and at least one arm 132 extending from the first side of the base 118. As illustrated in FIG. 7, at least two arms 132 extend from the first side of the base 118. The arms 132 as illustrated are positioned on opposed sides of the first side of the base 118 and spaced apart and extend generally upward from the base 118. The middle portion 130 encloses the space between the two arms 132 and consists of two semi-circular portions 180, whereby each semi-circular portion 180 of the middle portion 130 is disposed adjacent each arm 132. Each semi-circular portion 180 extends outward from a side of the arm 132 and follows an arcuate path to engage the side of the opposed arm 132. A first end of the semi-circular portion 180 is engaged to the first side of the base 118, and a right side and left side of the semi-circular portion 180 is engaged to the side of the arm 132. The second end of the semicircular portion 180 is angled downward in a parabolic shape.

The middle portion 130 is preferably hollow or has a central passageway for allowing light to progress through the middle portion 130. The arms 132 are spaced apart for allowing light to pass out of the top portion of the middle portion 130 and not obstructed by the arms 132. The upper portion of the arms 132 consist of a marking apparatus 136, such as that described above in the alternative embodiment.

Figure 8:
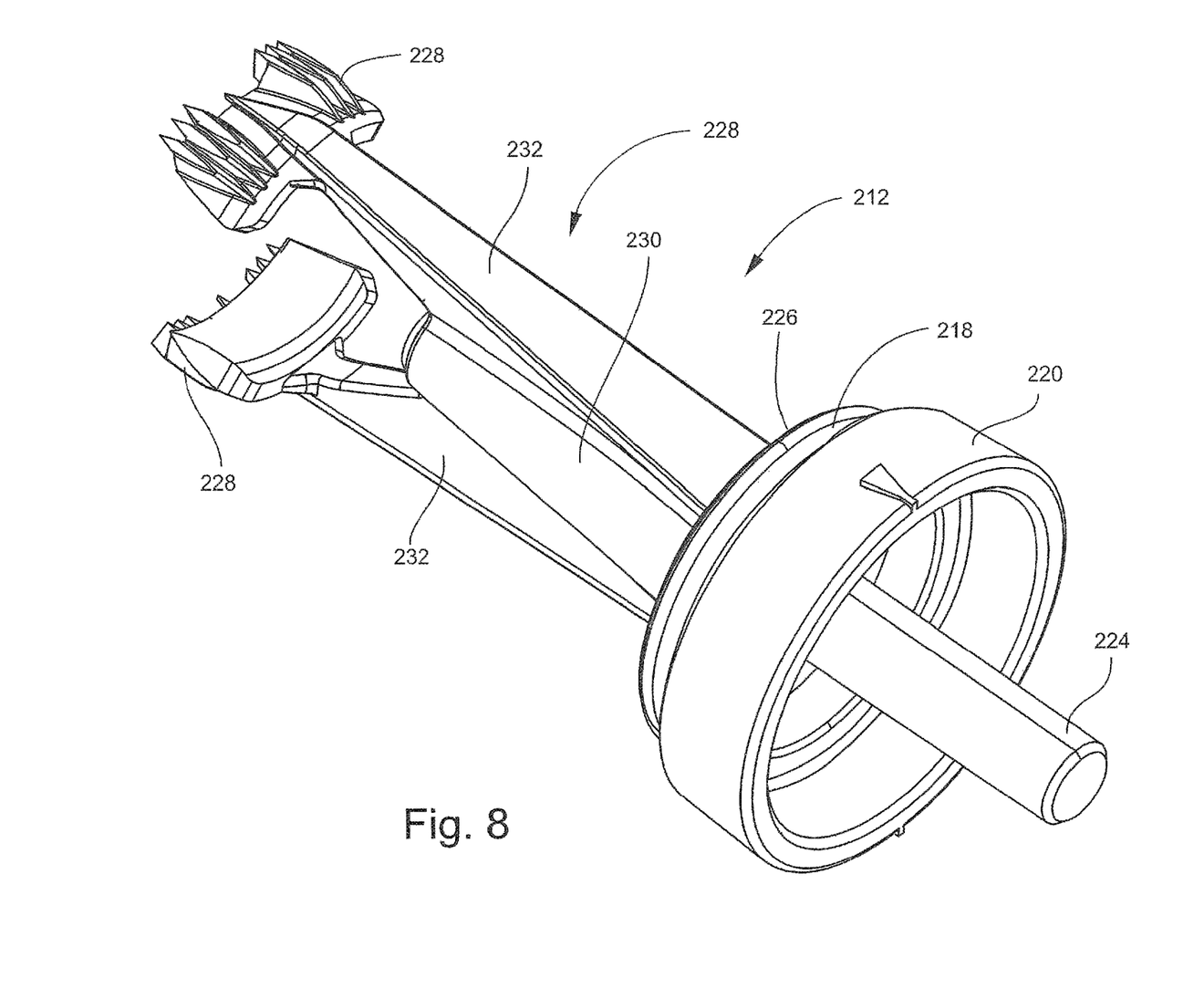
FIG. 8 is another perspective view of another embodiment of the tip.
Figure 9:
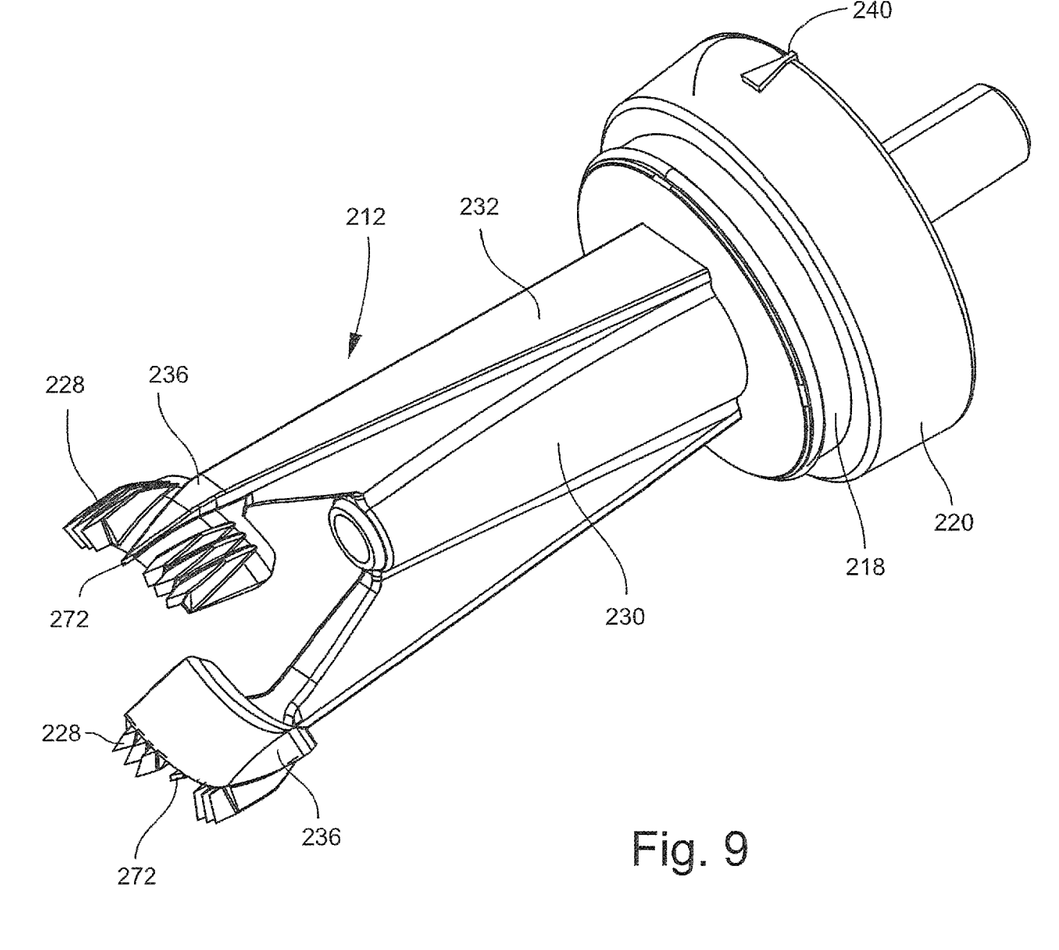
FIG. 9 is another perspective view of another embodiment of the tip.

In an alternative embodiment of the present invention as illustrated in FIGS. 8 and 9, the tip 212 comprises a base 218 with a first side and a second side that extends to an outer edge. An annular ring 220 having an interior side and exterior side is engaged to the outer edge of the base 218 and extending generally downward from the second side of the base 218 forming a cavity within the internal side of the annular ring and the bottom portion of the base 218. The external side of the base 218 comprises a rim 222 that circumscribes the external side of the base 218, extending generally upwardly from the external side of the base 218.

A post 224 extends from the base 218. The post 224 may be generally circular and hollow and having a top side and the bottom side. The top side of the post 224 is engaged to the second side of the base 218 and extending generally outward therefrom. The post 224 is preferably engaged to the central portion of the base 218. The base 218 may contain a centrally located bore 226 that extends from the first side to the second side of the base 218. The post 224 is engaged to the second side of the base 218 and overtop the bore 226 in the base 218 for allowing light to pass through the post 224 and proceed through the bore 226.

The tip 212 includes a marking means 228 is engaged to the first side of the base 218. The marking means 228 comprises a generally conical middle portion 230 and at least one arm 232 extending therefrom. As illustrated in FIGS. 8 and 9, at least two arms 232 extend from the middle portion 230 and extend outward from the middle portion 230 and extend above the middle portion 230. The arms 232 as illustrated are positioned on either side of the middle portion 230 and in a spaced apart relationship. The middle portion 230 is preferably hollow or has a central passageway for allowing light to progress through the middle portion 230. The middle portion 230 may be solid also. The middle portion 230 has a top portion and a bottom portion. The bottom portion of the middle portion 230 is engaged to the first side of the base and extends generally outward therefrom. As illustrated, the diameter of the middle portion gradually decreases from the bottom portion to the top portion. A lens 234 may optionally be positioned within a centrally located opening within the top portion of the middle portion 230 or be placed at the base of post 224.

The middle portion 230 contains an external side and an internal side. The arms 232 extend outwardly from the external side of the middle portion 230 and longitudinally upward and extending above the middle portion 230. The arms 232 are spaced apart for allowing light to pass out of the top portion of the middle portion 230 and not obstructed by the arms 232. The upper portion of the arms 232 consist of a marking apparatus 236. The upper portion of the arms 232 contain a generally square or generally rectangular marking apparatus 236 with raised ridges 272 extending along the backside and protruding over the marking apparatus 236. The ridges 272 extend to a point for making a mark on the eye. As illustrated in FIGS. 8 and 9, 6 ridges that extend to a point are contained on each marking apparatus 236. The points of the ridges 272 may be pre-inked for placing a mark on the cornea and may have one or more ridges 272, and preferably one to twelve ridges 272.

In yet another alternative embodiment, a tip 12 may not include the post (24, 124, 224) and the base (18, 118, 218) may extend elongately, allowing for the attachment of a cylindrical post 24. The cylindrical post 24 is engaged to a rotational scale 44 by either entering a circular deep groove in the face of the rotational scale 44 or by overlapping over the outside circumference of the rotational scale 44. When the rotational scale 44 is overlapping the outside circumference, a magnifying lens may be utilized with the cylinder to magnify the axis numbers of the rotational scale 44. Alternatively, the axis numbers could be provided on the base 18 of the tip 12.

In yet another alternative embodiment, the handle 16 contains a hub on the anterior end. The hub is generally circular in shape and has a diameter less than the diameter of the handle 16. The central bore of the rotational scale 44 is received within the hub forming a rotational engagement and the exterior side of the rotational scale 44 forms a shelf for receiving the outer edge of the outer circumference. The hub is received within the cavity of the tip 12 forming a selectively secured arrangement. The upper portion of the hub contains a chamfered portion to guide the hub into the cavity. The cavity of the tip 12 may be received as indicated above or may be received in a deep circular channel created on the face of and towards the outer circumference of rotational scale 44. In other words, the cavity of the tip 12 can be attached to the handle by a central post, a mid peripheral deep stabilization channel or by the outer circumference of rotational scale 44. In a related alternative embodiment, the above configuration may be reversed such that the axis scale is placed on base 18 which then is rotated to a indicator mark on rotational scale 44.

In another alternative embodiment of the present invention, the present invention may be utilized in a non-medical capacity. The device 10 provides a visual projected beam of light that reveals a desired angle position, which is achieved by replacing the LED 48 with a laser (not shown) and replacing the tip 12 with the optics that project the desired beam configuration. By way of example only, the projected laser beam can be a line that defines an angle of inclination for verifying angular positions in orthopedic surgery or the construction industry. If a particular implant or object is needed to be placed at a 45° angle, this angle would be entered into the display 58 with the servo motor 56 maintaining the projected laser line at 45° regardless of the position changes in the hand held device. This alternative embodiment would be useful in detecting various angles of previously constructed entities since the servo motor 56 could be disabled such that aligning the laser beam with an object of interest would change the position of the device 10 with a corresponding readout of the angular position.

In another alternative embodiment, the device 10 may also be alternatively equipped with other marking apparatus 36, including, but not limited to, one or more marking apparatus 36 or pads consisting of a plurality of shapes. Additionally, the marking apparatus 36 may consist of a plurality of shapes including, but not limited to, circles, squares, rectangles, trapezoids, shapes with one or more vertices or shapes having concave or convex geometries.

One purpose of the device 10 is to provide preoperative eye marks that can be placed at the desired axis of astigmatic correction with a high level of accuracy, and that can be placed well in advance of the surgery allowing optimal patient flow. The tip 12 may be disposable, so no sterilization is needed as with the reusable metal markers. The one use aspect avoids any sterilization issues and improves patient flow since there is no wait for sterilization to be accomplished. The tip 12 and sleeve 14 are designed to provide an inexpensive, sterilizable attachment that can be disposed of after use. The remainder of the device may or may not be sterilized between use.

The marking apparatus 36 may be modified to contain a channel or reservoir of dried or powdered ink/indicator. When the marking apparatus 36 contacts the moist cornea the indicator is hydrated and transferred to the cornea leaving lasting marks. All references to corneal marking could equally be applied to corneal scleral or scleral marking of the eye by way of simple configuration changes of the marking tip.

The marking apparatus 36 may be of any shape or configuration for placing a mark or indicator on the surface of the eye. The marking apparatus 36 may be composed of bonded fiber, porous plastic, a porous material such as paper, cork, expanded styrofoam, aerogels, or any like material that may be infused to hold or contain an indicator, pigment, ink, suspended ink fiber or suspended ink string. The tip 12 may be composed of plastic, and therefore, disposable. Alternatively, the tip 12 may be composed of metal or plastic so that it can be sterilized for repeated uses.

In another alternative embodiment of the present invention, the device 10 may contain a fixation device that is centrally disposed on the tip 12. Generally, the fixation device is positioned adjacent the hollow cavity of the post. The fixation device may include a fixation lens, fixation imprint, or a fixation target.

In yet another alternative embodiment of the present invention, the present invention may be adapted as an accessory that uses the position sensing electronics of portable devices 305, such as smart phones. During use, the desired degree axis is entered into the smart phone 305 via a downloadable application 396 that uses the computational power of the smart phone 305 to direct the servo motor 356. The rotational scale 344, servo motor 356, and LED 348 would be housed together in a manner that they would be engaged to the smart phone by one of many connection means commonly known to one of ordinary skill in the art, such as the female audio receptacle micro-USB or an Apple® micro USB adapter.

Figures 10, 11, 12:
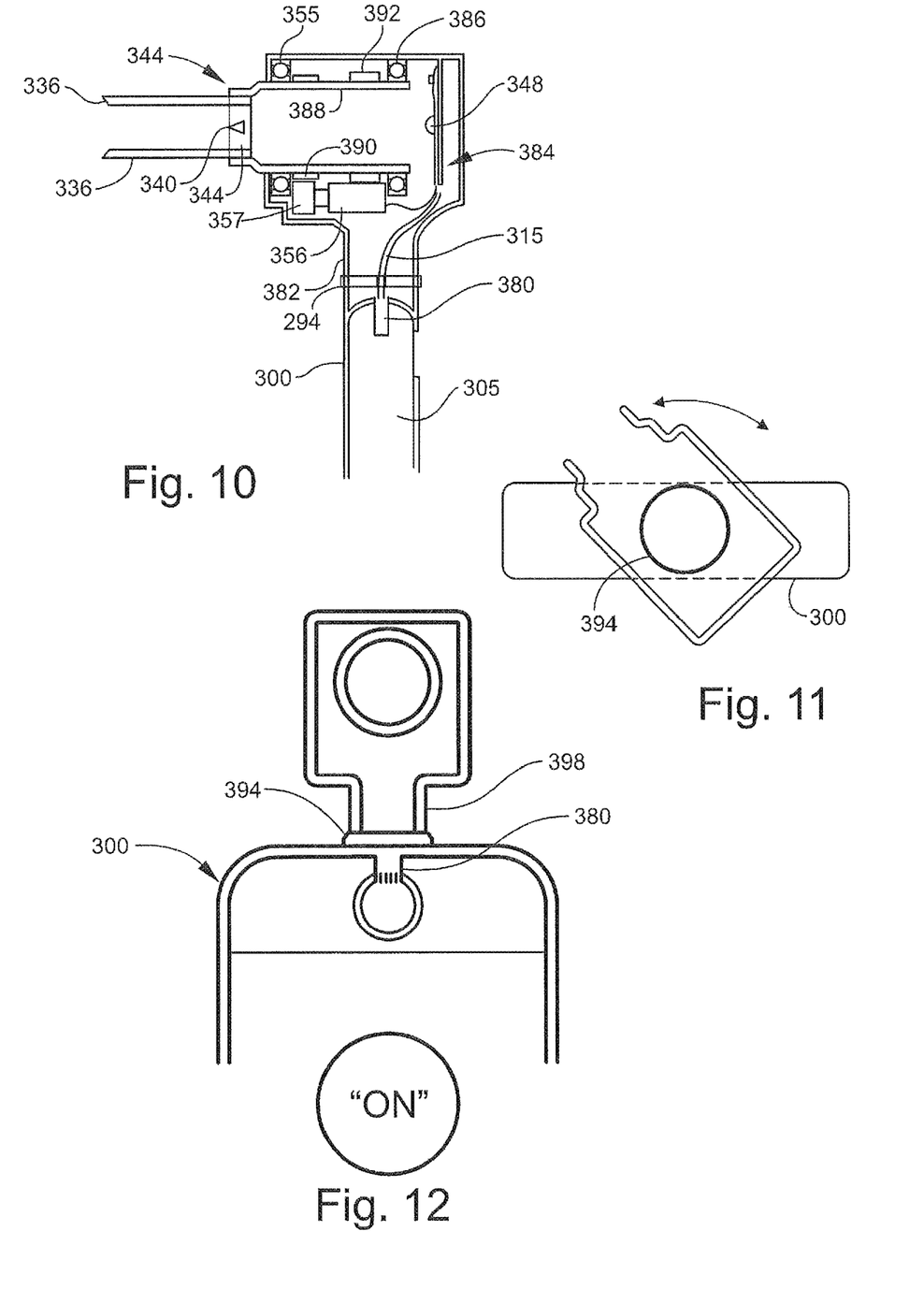
FIG. 10 is a side view of another embodiment of the eye marker device engaged to a portable electronic device.
FIG. 11 is a side view of the rotational turret of the eye marker device of FIG. 10.
FIG. 12 is a front view of the eye marker device of FIG. 10.

In another embodiment as illustrated in FIG. 10, an adaptor 300 is made for use in portable devices 305, such as smart phones, PDAs, handheld devices, tablets, and the like that does not require a servo motor mechanism. As illustrated in FIG. 10, the adapter 300 is engaged to a smart phone 305, but this is for illustrative purposes only and should not be construed as limiting. The adapter 300 includes an electrical plug 380 that is inserted into the smart phone 305. An electrical current flows from the smart phone 305, through the electrical plug 380, phone jack or USB, and through the wires 315 (housed within an: elongated housing 382 that protects the wires and spaces the adapter 300 from the surface of the smart phone 305) to the LED circuit 384. The LED circuit 384 is activated by a downloaded program 396, and provides illumination to marking apparatus 336 of the tip 312 through the hollow cylinder 388. The smart phone 305 contains a downloaded program 396 that is displayed on the screen of the smart phone 305. The downloaded program 396 uses the phone 305 position sensors to provide feedback as to the position of the phone 305 in one of two ways.

In one embodiment, the tip 312 is aligned with the position indicator 340 to the desired axis position on the rotational scale 344. The goal is to keep the smart phone 305 level horizontally with the application providing feedback means by displaying a solid green screen when the smart phone 305 is perfectly horizontal. When the smart phone 305 is within a range close to horizontal, the screen would blink green. When the position was a predetermined range "off" horizontal, the screen would blink a succession of colors to give the user visual feedback as to the severity of the position error. Different colors would be accompanied by different auditory feedback provided by the phone's 305 speakers.

In an alternative embodiment, the user could place the marker at zero degrees on rotational scale 344. The user would then use the screen of the smart phone 305 to enter the desired axis position for the marking apparatus 336 of the tip 312 with the application now providing visual and auditory feedback to confirm when the smart phone 305 had been rotated to that desired axis position.

The adaptor 300 includes an electrical plug 380 that is inserted into an orifice of the smart phone 305. The orifice may be the headphone jack, multi pin connector, the USB port, or the like. The electrical plug 380 of the adaptor 300 provides energy to the adaptor 300 and communicates with the smart phone 305. The electrical plug 380 may also contain a post on either side to prevent the electrical plug 380 from rotating within the orifice of the smart phone 305.

Alternatively, the servo motor 356 can be adapted to a smart phone 305 wherein the smart phone 305 provides positional/computational information and electricity that drives a servo mechanism housed within an adaptor 300. The adaptor 300 could also be provided with a separate battery source. The smart phone adaptor 300 includes ball bearings 355 and 386 to facilitate the rotation of the rotational scale 344 when rotated by servo motor 356 through servomotor gear 357 connected to rotational scale 344 360 by cylinder gear 390. If necessary, a counterbalance cylinder ring 392 can be attached to rotational scale 344 to insure that the lever arm weight of marking apparatus 336 is balanced relative to bearing 355 386 in order to promote effortless rotation of rotational scale 344 when activated by servo motor 356. Smart phone adaptor 300 may also be provided with rotational turret 394 to allow adaptor head 3 to rotate freely relative to smart phone 305.

Figures 13A, 13B, 14:
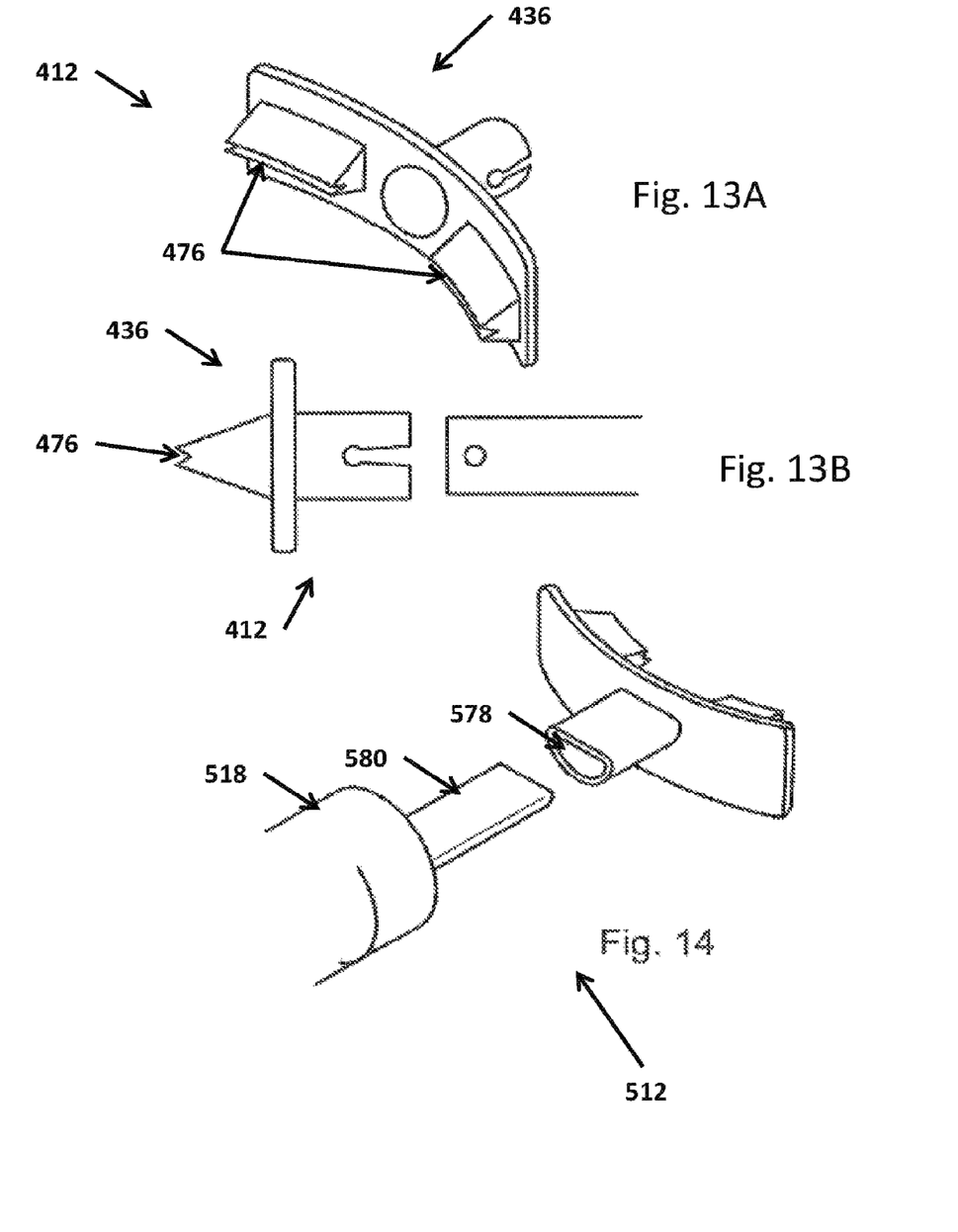
FIG. 13A is a perspective view of another alternative embodiment of the tip and FIG. 13B is a side view of the alternate embodiment of the tip of FIG. 13A.
FIG. 14 is a perspective view of another alternative embodiment of the tip.

In another alternative embodiment as illustrated in FIG. 13, the tip 412 may include a channel 476 that may be positioned on the upper portion of the arms 432, the marking means 428, or top portion of the middle portion 430. The channel 476 is designed to receive a marking apparatus 436. The marking apparatus 436 may place a mark or an indicator on the surface of the cornea, sclera, or the sclera/cornea junction (also collectively referred to as the surface of the eye). The marking apparatus 436 may be pre-inked, whereby the tip is infused with ink. Additionally, the marking apparatus 436 may apply a tack or other like indicator on the surface of the cornea, sclera, or the sclera/cornea junction. The marking apparatus 436 is designed to be received within the channel 476.

In another alternative embodiment as illustrated in FIG. 14, the tip 512 may consist a first part and a second part. The first part consists of a marking apparatus that contains a sleeve 578 or hollow channel. The second part of the tip 512 consists of a receiving portion 580 that may be engaged to the base 518. The sleeve 578 is a female portion and the receiving portion 580 is the male portion. The receiving portion 580 is received within the sleeve 578 in a selectively secured arrangement. The diameter of the sleeve 578 is slightly larger than the diameter of the receiving portion 580 and thereby held together by a friction fit. Alternatively the sleeve 578 may "snap on" the receiving portion 580 or be selectively engaged by other attachment means.

Although the present invention has been illustrated and described herein with reference to preferred embodiments and specific examples thereof, it will be readily apparent to those of ordinary skill in the art that other embodiments and examples may perform similar functions and/or achieve like results. All such equivalent embodiments and examples are within the spirit and scope of the present invention and are intended to be covered by the following claims.

That which is claimed is:

1. An eye marker tip comprising:
   a base comprising a first side and a second side, the base extending to an outer edge;
   a marking tip extending from the first side of the base, the marking tip comprising a hollow middle portion with a top portion and at least two arms extending to a distal end above the top portion of the hollow middle portion of the marking tip, wherein the at least two arms are in a spaced-apart relationship from each other and the at least two arms extend upward from the first side of the base and the hollow middle portion spans between the at least two arms and the at least two arms are dimensioned for placing at least one mark or indicator on a cornea, sclera or sclera/cornea junction of an eye;

a post extending from the second side of the base; and a light conducting passageway oriented substantially along a longitudinal axis of the eye marker tip from a distal end of the post through the hollow middle portion of the marking tip, thereby enabling light received at the distal end of the post to pass through the hollow middle portion of the marking tip;

wherein the at least two arms do not extend along all of a radius pivoting substantially about the longitudinal axis, thereby none of the at least two arms are substantially obstructing the light received at the distal end of the post and enabling a user to observe, along an axis not passing through the base, a target area on the longitudinal axis, proximate the distal end of the at least two arms.

2. The eye marker tip of claim 1, further comprising an annular ring having an internal side and an external side extending from the outer edge and forming a cavity within the internal side of the annular ring and a bottom portion of the base.

3. The eye marker tip of claim 1, further comprising a channel disposed on the at least two arms for receiving a marking apparatus comprising at least one ridge.

4. The eye marker tip of claim 3, wherein the ridge is undulated.

5. The eye marker tip of claim 3, wherein the ridge is smooth.

6. The eye marker tip of claim 1, wherein the light conducting passageway further extends through the at least two arms.

7. The eye marker tip of claim 1, wherein the hollow middle portion comprises two semi-circular portions disposed to adjacent each of the at least two arms.

8. The eye marker tip of claim 1, wherein the eye marker tip is disposable.

9. The eye marker tip of claim 1, wherein the marking tip is pre-inked by infusing with dried or powdered ink.

10. An eye marker device comprising:
a handle and
an eye marker tip comprising:
a base comprising a first side and a second side, the base extending to an outer edge;
a marking tip extending from the first side of the base, the marking tip comprising a hollow middle portion with a top portion and at least two arms extending to a distal end above the top portion of the hollow middle portion of the marking tip, wherein the at least two arms are in a spaced-apart relationship from each other and the at least two arms extend upward from the first side of the base and the hollow middle portion spans between the at least two arms and the at least two arms are dimensioned for placing at least one mark or indicator on a cornea, sclera or sclera/cornea junction of an eye; and
a post extending from the second side of the base; and
a light conducting passageway oriented substantially along a longitudinal axis of the eye marker tip from a distal end of the post through the hollow middle portion of the marking tip, thereby enabling light received at the distal end of the post to pass through the hollow middle portion of the marking tip;
wherein the at least two arms do not extend along all of a radius pivoting substantially about the longitudinal axis, thereby none of the at least two arms are substantially obstructing the light received at the distal end of the post and enabling a user to observe, along an axis not passing through the base, a target area on the longitudinal axis, proximate the distal end of the at least two arms.

11. The eye marker tip of claim 10, wherein the eye marker tip and the handle are for single use.

12. The eye marker tip of claim 10, wherein the eye marker tip is disposable and the handle is reusable.

13. The eye marker device of claim 10, further comprising an LED.

14. The eye marker device of claim 13, wherein the LED is an ANSI eye safe laser and provides a projection through the light conducting passageway to enable a user to know where the at least one or more mark or indicator will be placed on the cornea of the eye.

* * * * *